United States Patent
Hwang et al.

(10) Patent No.: US 8,598,372 B2
(45) Date of Patent: Dec. 3, 2013

(54) METHOD FOR PRODUCING CYCLICISED COMPOUNDS FROM ORGANIC ACIDS HAVING FROM 4 TO 6 CARBON ATOMS

(75) Inventors: Young Kyu Hwang, Daejeon (KR); Jong San Chang, Daejeon (KR); Jung Ho Lee, Daejeon (KR); Jong-Min Lee, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 13/395,168

(22) PCT Filed: Aug. 27, 2010

(86) PCT No.: PCT/KR2010/005770
§ 371 (c)(1),
(2), (4) Date: Apr. 5, 2012

(87) PCT Pub. No.: WO2011/031023
PCT Pub. Date: Mar. 17, 2011

(65) Prior Publication Data
US 2012/0197029 A1 Aug. 2, 2012

(30) Foreign Application Priority Data

Sep. 11, 2009 (KR) .......................... 10-2009-0085883
Aug. 17, 2010 (KR) .......................... 10-2010-0079084

(51) Int. Cl.
C07D 313/00 (2006.01)
C07D 307/00 (2006.01)
C07D 307/02 (2006.01)

(52) U.S. Cl.
USPC ............................ 549/266; 549/326; 549/508

(58) Field of Classification Search
USPC ........................................ 549/266, 326, 508
See application file for complete search history.

(56) References Cited

U.S. PATENT DOCUMENTS 2,786,852 A * 3/1957 Dunlop et al. ................. 549/326
4,420,622 A * 12/1983 van de Moesdijk et al. .. 549/326
5,883,266 A 3/1999 Elliott et al.
6,617,464 B2 * 9/2003 Manzer ......................... 549/326

OTHER PUBLICATIONS

Upare et al. ChemSusChem 2011, 4, 1749-1752.*
Dorwald F. A. Side Reactions in Organic Synthesis, 2005, Wiley: VCH, Weinheim p. IX of Preface p. 1-15.*

* cited by examiner

Primary Examiner — Nizal Chandrakumar
(74) Attorney, Agent, or Firm — Sughrue Mion, PLLC

(57) ABSTRACT

The present invention relates to a method for producing a cyclic compound that has high selectivity, high yield, and stability over a long period of time depending on a metal content ratio of a catalyst, specifically a lactone compound or a heterocyclic compound including oxygen, which includes hydrogenating an organic acid, organic acid ester, or a mixture of the organic acid and organic acid ester, which are having 4 to 6 carbon atoms, by using a selective hydrogenated catalyst.

8 Claims, No Drawings

METHOD FOR PRODUCING CYCLICISED COMPOUNDS FROM ORGANIC ACIDS HAVING FROM 4 TO 6 CARBON ATOMS

TECHNICAL FIELD

The present invention relates to a method for producing a cyclic compound that has high selectivity, high yield, and stability over a long period of time depending on a metal content in catalyst, specifically, a lactone compounds or a heterocyclic compounds including oxygen, which includes hydrogenating an organic acid, organic acid ester, or a mixture of the organic acid and organic acid ester, which are having 4 to 6 carbon atoms, by using a selective hydrogenated catalyst.

BACKGROUND ART

A method for producing gamma-valerolactone (GVL) and 2-methyltetrahydrofuran by gas phase and liquid phase hydrogenating a levulinic acid under a catalyst is mainly used as a general method for producing gamma-valerolactone (GVL) and 2-methyltetrahydrofuran, and more economical catalysts and processes have been used.

A catalyst including precious metal as a main component is mostly used as a catalyst hydrogenating the levulinic acid to manufacture 2-methyltetrahydrofuran. For example, U.S. Pat. No. 5,883,266 shows high yield with a Pd—Re-based catalyst, and in U.S. Pat. No. 6,045,611, 2-methyltetrahydrofuran is obtained at a relatively high yield by using a catalyst phase made of Ni, Co, Al, or Zr oxides as a catalyst not using precious metal. However, there is a problem in that all are operated at a high hydrogen pressure.

Further, precious metal is mainly used as the catalyst manufacturing gamma-valerolactone (GVL) from the levulinic acid to obtain high yield. For example, in U.S. Patent Laid-Open Publication No. 2003/0055270 and WO 2002/074760, Ru, Pd, Rh, and Pt are carried in Carbon, $SiO_2$, $TiO_2$, $Al_2O_3$, and zeolites to obtain high yield, and in a document by Applied Cat. A general, 272(2004), 249, a process of obtaining high yield by using a 5% Ru/carbon catalyst has been developed. However, problems are found in view of economic efficiency and stability in that the main component of the catalysts used in the aforementioned process is precious metal and operation is performed at a relatively high hydrogen pressure.

DISCLOSURE

Technical Problem

Therefore, the present inventors developed a hydrogenated catalyst process that is more economical and exhibits high productivity in a low pressure condition, excellent catalyst stability over a long period of time, and a low environmental load as compared to a process using precious metal by applying a copper oxide-silica nanocomposite as a selective hydrogenated catalyst in order to prevent an economical problem of a precious metal catalyst of a known process for producing a cyclic compound, specifically, a lactone compounds such as gamma-valerolactone, 2-methyltetrahydrofuran and a heterocyclic compound including oxygen, from an organic acid including a levulinic acid, organic acid ester, or a mixture of the organic acid and organic acid ester, which are having 4 to 6 carbon atoms, and problems regarding a production method at a high hydrogen pressure, and also developed a catalyst for producing a lactone compound and a cyclic compound such as gamma-valerolactone, angelica lactone, tetrahydromethylfuran, caprolactone, and gamma-butyllactone including oxygen by controlling a ratio of copper oxide and silica.

Accordingly, an object of the present invention is to provide a method for producing a cyclic compound, specifically a lactone compound and a heterocyclic compound including oxygen, by hydrogenating an organic acid, organic acid ester, or a mixture of the organic acid and organic acid ester, which are having 4 to 6 carbon atoms, by using a nano-sized copper oxide-silica complex as a selective hydrogenated catalyst. Further, there is provided a method for producing a heterocyclic compound by hydrogenating a biomass-derived organic acid from cellulose, hemicellulose, and glucose and an ester compound thereof.

Technical Solution

In order to accomplish the aforementioned objects, the present invention provides a method for producing a cyclic compound, which satisfies the following specific conditions and includes directly reducing an organic acid, organic acid ester, or a mixture of the organic acid and organic acid ester, which are having 4 to 6 carbon atoms, by a gas phase hydrogenation reaction on a copper-based nanocomposite catalyst.

In the present invention, the copper-based nanocomposite catalyst includes copper-silica as main components.

Specifically, the present invention is a method for producing a cyclic compound, which includes performing direct gas phase reduction of an organic acid, organic acid ester (e.g.: biomass-derived dimethyl succinate, methyl levulinate, dimethyl glutarate, dimethyl asparate, and the like), or a mixture of the organic acid and organic acid ester by hydrogen on a reduced copper-based catalyst, and the reduced copper-based catalyst may be modified by further including one or more conditioning components selected from the group consisting of cobalt, nickel, zinc, chromium, manganese, ruthenium, rhenium, palladium, platinum, silver, tellurium, selenium, magnesium, and calcium.

The present invention relates to a method for producing a cyclic compound, which includes performing direct gas phase reduction of an organic acid, organic acid ester, or a mixture of the organic acid and organic acid ester, which are having 4 to 6 carbon atoms, by hydrogen on a copper-based catalyst and, specifically, the cyclic compound is a lactone compound and a heterocyclic compound including oxygen. Further, there is provided a method for producing a heterocyclic compound by hydrogenating a biomass-derived organic acid such as cellulose, hemicellulose, and glucose, organic acid ester, or the mixture of the organic acid and organic acid ester.

This becomes more apparent when considering that the hydrogenation reaction of the organic acid, organic acid ester, or the mixture of the organic acid and organic acid ester, which are having 4 to 6 carbon atoms, is performed at a reaction temperature of 200 to 350° C. but diffusion of copper nanoparitices that are the main components of the catalyst starts at about 180° C. [Reference document: Topics in Catalysis 8 (1999) 259]. Accordingly, in the case where the catalyst used in the present invention is produced by a carrying method, efficiency is reduced, and it is effective to perform the production by a coprecipitation method or a sol-gel method to obtain a synergic effect.

In the present invention, it is preferable that the catalyst has a neutral property to obtain high selectivity by suppressing a dehydration reaction of the organic acid, organic acid ester, or the mixture of the organic acid and organic acid ester, which are having 4 to 6 carbon atoms, that are products when considering that the hydrogenation reaction of the organic acid, organic acid ester, or the mixture of the organic acid and organic acid ester, which are having 4 to 6 carbon atoms, is performed at 200° C. or more and specifically 200 to 350° C., and, accordingly, a copper-silica nanocomposite catalyst including nanoparticles of silica as a diluting agent in the copper-based catalyst is useful to accomplish the objects of the present invention.

A weight ratio of a copper oxide (CuO) component to silica ($SiO_2$) of the copper-based catalyst is 0.1:99.9 to 99:1. In the case where the cyclic compound is the lactone compound, the weight ratio of the copper oxide (CuO) component to silica ($SiO_2$) of the copper-based catalyst is 5:95 to 70:30, in the case where the cyclic compound is the heterocyclic compound including oxygen, the weight ratio of the copper oxide (CuO) component to silica ($SiO_2$) of the copper-based catalyst is 9:1 to 4:6, and the copper-based catalyst is a catalyst produced to have a particle size of copper oxide of 50 nm or less. The silica is not a typical carrier of the catalyst but nano-sized fine particles, and subjected to nanocomposite in conjunction with the copper component to suppress movement of the copper nanoparticles, thus allowing the catalyst to have thermal stability.

In the case where the gas phase hydrogenation reaction of the organic acid, organic acid ester, or the mixture of the organic acid and organic acid ester, which are having 4 to 6 carbon atoms, is performed on the copper-based catalyst having the above properties, unlike the aforementioned patent documents disclosing indispensable use of water, the direct hydrogenation of the organic acid, organic acid ester, or the mixture of the organic acid and organic acid ester, which are having 4 to 6 carbon atoms, may be performed without water to obtain the lactone compound and the heterocyclic compound including oxygen that are the cyclic compound with high productivity and high yield.

The organic acid having 4 to 6 carbon atoms is selected from the group consisting of a levulinic acid, a succinic acid, a fumaric acid, an itaconic acid, an aspartic acid, an adipic acid, and a glucaric acid, and preferably selected from the levulinic acid, the succinic acid, the fumaric acid, and the adipic acid.

In the case where the organic acid is the levulinic acid, gamma-valerolactone (GVL) and 2-methyltetrahydrofuran are obtained as the cyclic compound that is the product of the hydrogenation reaction, in the case where the organic acid is the succinic acid or the fumaric acid, butyrolactone and tetrahydrofuran are obtained as the cyclic compound, in the case where the organic acid is the itaconic acid, 3-methylbutyrolactone and 3-methyltetrahydrofuran are obtained as the cyclic compound, in the case where the organic acid is aspartic acid, aspartic anhydride and 3-aminotetrahydrofuran are obtained as the cyclic compound, in the case where the organic acid is the adipic acid, ε-caprolactone and oxepane are obtained as the cyclic compound, and in the case where the organic acid is the glucaric acid, glucaro-δ-lactone and glucaro-γ-lactone are obtained as the cyclic compound.

In the present invention, the gas phase hydrogenation reaction of the organic acid, organic acid ester, or the mixture of the organic acid and organic acid ester, which are having 4 to 6 carbon atoms, is performed on the catalyst in the condition of the aforementioned reaction temperature and the reaction pressure of 0.5 to 50 atm, and a conversion ratio is low in the case where the pressure is low and an excessive amount of hydrogen should be used to maintain a gas phase state of the organic acid, organic acid ester, or the mixture of the organic acid and organic acid ester, which are having 4 to 6 carbon atoms, in the case where the pressure is high, which are not preferable. Further, a liquid hourly space velocity (LHSV) of the organic acid having 4 to 6 carbon atoms is 0.05 to 10 $h^{-1}$.

It is more effective to use the catalyst modified by at least one or more components from components such as cobalt, zinc, chromium, manganese, ruthenium, rhenium, palladium, platinum, silver, tellurium, selenium, magnesium, and calcium as a conditioning component in order to more preferably increase a hydrogenation ability in conjunction with the copper component and suppress decarboxylation. It is preferable to use the conditioning agent component in the content of 50 wt % or less based on the content of copper oxide, and when the conditioning agent component is used in an excessive amount, performance of the catalyst is reduced.

In the method for producing the lactone compound and heterocyclic compound including oxygen that are the cyclic compound of the present invention, the catalyst is typically produced in a complex oxide form to be filled in a reactor, and subjected to an activation process of reducing the catalyst by increasing a temperature to 150 to 400° C. and preferably 200 to 350° C. under a hydrogen gas flow diluted by nitrogen before a reduction reaction is performed.

Advantageous Effects

A method for producing a lactone compound and a heterocyclic compound including oxygen that are a cyclic compound by hydrogenating an organic acid, organic acid ester, or a mixture of the organic acid and organic acid ester, which are having 4 to 6 carbon atoms, by a specific catalyst according to the present invention is advantageous in that the method is more economical and exhibits high productivity in a low pressure condition, excellent catalyst stability over a long period of time, and a low environmental load as compared to a known process using precious metal by using a nano-sized copper oxide-silica nanocomposite as a selective hydrogenated catalyst.

BEST MODE

A better understanding of the present invention may be obtained in light of the following examples which are set forth to illustrate, but are not to be construed to limit the present invention.

Example 1

Production of 2-Methyltetrahydrofuran from the Levulinic Acid Through the Hydrogenation Reaction [Catalyst: CuO(80)$SiO_2$(20)]

Solution A where 50 g of copper nitrate [$Cu(NO_3)_2 \cdot 3H_2O$] was dissolved in 200 ml of deionized water was prepared. The sodium hydroxide aqueous solution was added to 100 ml of deionized water to adjust the pH to 9.2 and 13.75 g of colloidal silica Ludox SM-30 was applied thereto to prepare solution B, and solution C where 16.6 g of sodium hydroxide was dissolved in 200 ml of deionized water was prepared. Solutions A, B, and C were simultaneously applied in drops to the reactor with the agitator to perform the precipitation process at 20° C. or less. Thereafter, the obtained slurry solution was agitated at normal temperature for 12 hours and then subjected to hydrothermal aging for 6 hours while being heated to 85° C. The obtained slurry was sufficiently washed with deionized water and filtered, and the obtained cake was dried at 120° C. for 12 hours and then powderized.

The obtained powder was subjected to compression molding, pulverized to have the size of 20 to 40 meshes, fractionated, and fired in an air atmosphere at 600° C. for 6 hours to obtain the catalyst in an oxide state. The particle size of copper oxide of the catalyst was 5 nm, as a result of measuring by the XRD line broadening method. 1.0 g of the catalyst was charged in the tube type reactor (ID=6.35 mm), and the temperature was increased to 280° C. while the $N_2$ gas including 5% $H_2$ was flowed to activate the catalyst. Thereafter, the pressure of the reactor was adjusted to 370 psi (25 bar) at various reaction temperatures, and the reaction depending on each temperature was performed while the solution where the levulinic acid was dissolved in 1,4-dioxane (levulinic acid: 1,4-dioxane=10:90 w/w) was supplied at a rate of 0.9 cc/hr under a hydrogen gas flow at 130 ml/min. The experiment results are described in the following Table 1, and the catalyst of the present invention exhibited the highest selectivity at 265° C.

TABLE 1

| Temp (° C.) | Conv. (%) | MTHF[1] | 1-pentanol | Angelica lactone | GVL[2] | 1,4-PDO[3] |
|---|---|---|---|---|---|---|
| | | | | Selectivity (%) | | |
| 200 | 100 | 5 | 0.6 | 0 | 50 | 45 |
| 230 | 100 | 30 | 8 | 5 | 43 | 15 |
| 265 | 100 | 53 | 46 | 0.5 | 0.4 | 0 |
| 290 | 100 | 50 | 49 | 0 | 0 | 1.2 |
| 330 | 100 | 35 | 63 | 0.2 | 0 | 2 |

[1]Methyltetrahydrofuran
[2]Gamma-valerolactone
[3]1,4-propanediol

Example 2

Production of 2-Methyltetrahydrofuran from the Levulinic Acid Through the Hydrogenation Reaction [Catalyst: CuO(80)SiO$_2$(20)]

The catalyst was produced by using the same method as Example 1. The reaction was performed by using the same method as Example 1, except that the temperature of the reactor was fixed to 265° C. and the pressure varied, and the results are described in the following Table 2. The catalyst of the present invention exhibited the highest selectivity at 20 bar.

TABLE 2

| Press. (bar) | Conv. (%) | MTHF[1] | 1-pentanol | Angelica lactone | GVL[2] | 1,4-PDO[3] |
|---|---|---|---|---|---|---|
| | | | | Selectivity (%) | | |
| 25 | 100 | 53 | 46 | 0.5 | 0.4 | 0 |
| 20 | 100 | 58 | 42 | 0 | 0 | 0 |
| 10 | 100 | 36 | 41 | 11 | 11 | 0.8 |

[1]Methyltetrahydrofuran
[2]Gamma-valerolactone
[3]1,4-propanediol

Example 3

Production of 2-Methyltetrahydrofuran from the Levulinic Acid Through the Hydrogenation Reaction [Catalyst: CuO(50)SiO$_2$(50)]

The catalyst was produced by using the same method as Example 1. The reaction was performed by using the same method as Example 1, while the production was performed so that the ratio of copper oxide was 50% based on the ratio of the copper oxide-silica nanocomposite and the reaction temperature was fixed to 265° C., and the results are described in the following Table 3.

TABLE 3

| Cat. | Conv. (%) | MTHF[1] | 1-pentanol | Angelica lactone | GVL[2] | 1,4-PDO[3] |
|---|---|---|---|---|---|---|
| | | | | Selectivity (%) | | |
| 80% CuO/SiO$_2$ | 100 | 53 | 46 | 0.5 | 0.4 | 0 |
| 50% CuO/SiO$_2$ | 100 | 43 | 51 | 0 | 1 | 5 |
| 30% CuO/SiO$_2$ | 100 | 3 | 10 | 5 | 63 | 20 |

[1]Methyltetrahydrofuran
[2]Gamma-valerolactone
[3]1,4-propanediol

Example 4

Production of Gamma-Valerolactone (GVL) from the Levulinic Acid Through the Hydrogenation Reaction The catalyst was produced by using the same method as Example 1. After copper oxides were produced in the ratio of 5%, 10%, and 30% based on the ratio of the copper oxide-silica complex and calcined at 600° C., 1.0 g of the catalyst was charged in the tube type reactor and activated by using the same method as Example 1. Thereafter, the temperature and the pressure of the reactor were adjusted to 265° C. and bar, the reaction depending on each temperature was performed while the solution where the levulinic acid was dissolved in 1,4-dioxane (levulinic acid: 1,4-dioxane=10:90 w/w) was supplied at a rate of 0.9 cc/h under a hydrogen gas flow at 130 ml/min, and the results are described in the following Table 4. As a result of the reaction, gamma-valerolactone was obtained with selectivity of 93% and the conversion of 100% by the 5% CuO/SiO$_2$ catalyst.

TABLE 4

| Cat. | Conv. (%) | MTHF[1] | 1-pentanol | Angelica lactone | GVL[2] | 1,4-PDO[3] |
|---|---|---|---|---|---|---|
| | | | | Selectivity (%) | | |
| 30% CuO/SiO$_2$ | 100 | 3 | 10 | 5 | 63 | 20 |
| 10% CuO/SiO$_2$ | 100 | 1 | 0 | 0.7 | 89 | 9 |
| 5% CuO/SiO$_2$ | 100 | 0.5 | 0 | 1.3 | 93 | 5 |

[1]Methyltetrahydrofuran
[2]Gamma-valerolactone
[3]1,4-propanediol

Example 5

Production of 2-Methyltetrahydrofuran from the Levulinic Acid Through the Hydrogenation Reaction [Catalyst: 80%(Cu$O_{0.9}$Ni$O_{0.1}$)/SiO$_2$]

The catalyst was produced by using the same method as Example 1. The 80% complex of copper oxide and nickel oxide was manufactured and used instead of copper oxide.

The temperature and the pressure of the reactor were fixed to 265° C. and 25 bar, respectively, and the reaction was performed by using the same method as Example 1. The results are described in the following Table 5.

TABLE 5

| Cat. | Conv. (%) | Selectivity (%) | | | | |
|---|---|---|---|---|---|---|
| | | MTHF[1] | 1-pentanol | Angelica lactone | GVL[2] | 1,4-PDO[3] |
| 80% (CuO$_{0.9}$NiO$_{0.1}$)/ SiO$_2$[4] | 100 | 91.4 | 0 | 0 | 0 | 0 |

[1]Methyltetrahydrofuran
[2]Gamma-valerolactone
[3]1,4-propanediol
[4]The balance 8.6% is butane.

As confirmed through Table 5, the conversion of the levulinic acid in the present Example was 100%, and the catalyst exhibited very high selectivity of 91.4% to 2-methyltetrahydrofuran.

Example 6

Production of 2-Methyltetrahydrofuran from the Levulinic Acid Through the Hydrogenation Reaction [Catalyst: 80%(CuO$_{0.95}$Co$_{0.05}$)/SiO$_2$]

The catalyst was produced by using the same method as Example 1. The 80% complex of copper oxide and cobalt was manufactured and used instead of copper oxide. The temperature and the pressure of the reactor were fixed to 265° C. and 25 bar, respectively, and the reaction was performed by using the same method as Example 1. The results are described in the following Table 6.

TABLE 6

| Cat. | Conv. (%) | Selectivity (%) | | | | |
|---|---|---|---|---|---|---|
| | | MTHF[1] | 1-pentanol | Angelica lactone | GVL[2] | 1,4-PDO[3] |
| 80% (CuO$_{0.95}$Co$_{0.05}$)/ SiO$_2$ | 100 | 70.7 | 21.2 | 0.6 | 7.5 | 0 |

[1]Methyltetrahydrofuran
[2]Gamma-valerolactone
[3]1,4-propanediol

As confirmed through Table 6, the conversion of the levulinic acid in the present Example was 100%, and the catalyst exhibited high selectivity of 70.7% to 2-methyltetrahydrofuran.

Example 7

Production of Gamma-Valerolactone (GVL) from the Levulinic Acid Through the Hydrogenation Reaction [Catalyst: CuO(5)SiO$_2$(95)]

The catalyst was produced by using the same method as Example 1. The production was performed so that the ratio of copper oxide was 5% based on the ratio of the copper oxide-silica complex, the reaction was performed by using the same method as Example 1 at the reaction temperature of 265° C. for each pressure condition, and the reaction results are described in the following Table 7. The present catalyst exhibited the highest selectivity at the reaction pressure of 10 bar.

TABLE 7

| Press. (bar) | Conv. (%) | Selectivity (%) | | | | |
|---|---|---|---|---|---|---|
| | | MTHF[1] | 1-pentanol | Angelica lactone | GVL[2] | 1,4-PDO[3] |
| 25 | 100 | 0.5 | 0 | 1.3 | 93 | 5 |
| 10 | 100 | 0.1 | 0 | 0 | 99.9 | 0 |
| 1 | 100 | 0 | 0 | 6.2 (alfa-) | 93.7 | 0 |

[1]Methyltetrahydrofuran
[2]Gamma-valerolactone
[3]1,4-propanediol

Example 8

Production of Butyrolactone from the Fumaric Acid Through the Hydrogenation Reaction [Catalyst: CuO(80)SiO$_2$(20)]

The catalyst was produced by using the same method as Example 1. The reaction temperature was fixed to 200° C., the reaction was performed by using the same method as Example 1, and the reaction results over time are described in the following Table 8. It could be observed that the present catalyst exhibited very high selectivity of butyrolactone after a predetermined period of time.

TABLE 8

| Time | Conv. (%) | Selectivity (%) | |
|---|---|---|---|
| | | Other | Butyrolactone |
| 4 | 100 | 4.6 | 95.4 |
| 12 | 100 | 7.5 | 92.5 |
| 16 | 100 | 5.6 | 94.4 |

※Feed condition: Fumaric:Hydrogen = (1:70), WHSV = 0.37 g/h, pressure = 25 bar, Feed = 5% in ethanol Example 9

Production of ε-Caprolactone from the Adipic Acid Through the Hydrogenation Reaction [Catalyst: CuO(80)SiO$_2$(20)]

The catalyst was produced by using the same method as Example 1. The reaction temperature was fixed to 265° C., the reaction was performed by using the same method as Example 1, and the reaction results over time are described in the following Table 7. The present catalyst exhibited high selectivity of 86.5% of ε-caprolactone.

TABLE 9

| Time | Conve. (%) | Selectivity (%) | | | | | |
|---|---|---|---|---|---|---|---|
| | | Cyclopentanone | Pentanoic acid | Hexanoic acid | ε-caprolactone | 1,6 hexanediol | ε-hydroxyl caproic acid |
| 8 | 98.5 | 1.1 | 6.1 | 1.7 | 15.3 | 73.4 | 0.8 |
| 30 | 98.0 | 6.0 | 2.5 | 2.2 | 83.3 | 1.0 | 2.8 |
| 62 | 98.0 | 6.9 | 2.5 | 1.4 | 82.1 | 0.8 | 4.0 |
| 74 | 97.0 | 1.7 | 4.0 | 2.9 | 86.5 | 0.7 | 1.0 |

※ Reaction condition: temperature = 265° C., pressure = 25 bar., WHSV = 0.428 g/h, $H_2$/Hydrogen = 80

Example 10

Production of 2-Methyltetrahydrofuran from the Levulinic Acid Through the Hydrogenation Reaction [Catalyst: CuO(80)SiO$_2$(10)TiO$_2$(10)]

The catalyst was produced by using the same method as Example 1. However, titanium(IV) isopropoxide was used as the TiO$_2$ component acting as the precursor, and dissolved in isopropanol for use. The particle size of copper oxide of the catalyst calcined at 600° C. was 15 nm. 1.0 g of the catalyst was charged in the tube type reactor and activated by using the same method as Example 1, and the reaction was performed in the same condition. As a result of the reaction, the conversion of levulinic acid over CuO(80)SiO$_2$(10)TiO$_2$(10)] was 99%, and the selectivity of 2-methyltetrahydrofuran was 50%.

Example 11

Production of Butyrolactone from the Fumaric Acid Through the Hydrogenation Reaction [Catalyst: CuO(80)SiO$_2$(20)]

The catalyst was produced by using the same method as Example 1. The fumaric acid was used instead of the levulinic acid as the reactant, the temperature and the pressure of the reactor were fixed to 265° C. and 25 bar, respectively, and the reaction was performed by using the same method as Example 1. The results are described in the following Table 10.

TABLE 10

| Cat. | Conv. (%) | Selectivity (%) | | | |
|---|---|---|---|---|---|
| | | Butyrolactone | 1,4-butanediol | Succinic acid | Others[2] |
| 80% CuO/SiO$_2$[1] | 100 | 65 | 10 | 20 | 5 |

[1]Reaction condition: temperature 265° C., pressure 25 bar, $H_2$/Fumaric acid = 70
[2]Others: Unknown compound As confirmed through Table 10, the conversion of fumaric acid over CuO(80)SiO$_2$(20) was 100%, and the catalyst exhibited very high selectivity of 65% to butyrolactone.

Example 12

Production of ε-Caprolactone from the Adipic Acid Through the Hydrogenation Reaction [Catalyst: CuO(80)SiO$_2$(20)]

The catalyst was produced by using the same method as Example 1. The adipic acid was used instead of the levulinic acid as the reactant, the temperature and the pressure of the reactor were fixed to 265° C. and 25 bar, respectively, and the reaction was performed by using the same method as Example 1. The results are described in the following Table 11.

TABLE 11

| Cat. | Conv. (%) | Selectivity (%) | | | | |
|---|---|---|---|---|---|---|
| | | ε-caprolactone | Cyclopentanone | Hexanoic acid | 1,6-hexanediol | Other products[2] |
| 80% CuO/SiO$_2$[1] | 100 | 80.2 | 5.5 | 4.2 | 1.8 | 8.3 |

[1]Reaction condition: temperature 265° C., pressure 25 bar, $H_2$/Adipic acid = 70, at 30 h
[2]Other products: E-hydroxylcarproic acid As confirmed through Table 11, the conversion of adipic acid was 100%, and the catalyst exhibited very high selectivity of 80% or more to ε-caprolactone.

The invention claimed is:

1. A method for producing a cyclic compound, comprising:
performing direct gas phase reduction of an organic acid by hydrogen on a copper-silica nanocomposite catalyst,
wherein the cyclic compound is selected from the group consisting of gamma-valerolactone, butyrolactone, ε-caprolactone, and 2-methyltetrahydrofuran,
the organic acid is selected from the group consisting of a levulinic acid, a fumaric acid, and an adipic acid, and
the copper-silica nanocomposite catalyst comprises a copper oxide and silica, wherein a weight ratio of the copper oxide to silica is 0.1:99.9 to 99:1.

2. The method of claim 1, wherein when the cyclic compound is butyrolactone, ε-caprolactone, and 2-methyltetrahydrofuran; and the weight ratio of the copper oxide to silica of the copper-catalyst is 80:20~50:50.

3. The method of claim 1, wherein when the cyclic compound is gamma-valerolactone; and the weight ratio of the copper oxide to silica of the copper-silica nanocomposite catalyst is 5:95 to 30:70.

4. The method of claim 1, wherein when the organic acid is levulinic acid; and the cyclic compound is gamma-valerolactone and 2-methyltetrahydrofuran.

5. The method of claim 1, wherein the catalyst further comprising one or more conditioning components selected from the group consisting of cobalt, nickel, zinc, chromium, manganese, ruthenium, rhenium, palladium, platinum, silver, tellurium, selenium, magnesium, and calcium.

6. The method of claim 1, wherein the organic acid is subjected to the gas phase reduction at a reaction temperature of 200 to 350° C. and a reaction pressure of 0.1 to 50 atm.

7. The method of claim 1, wherein a liquid hourly space velocity of the organic acid is 0.05 to 10 $h^{-1}$.

8. The method of claim 1, wherein complex oxides for manufacturing the copper-silica nanocomposite catalyst are reduced in a hydrogen gas flow diluted by nitrogen at a temperature of 200 to 350° C. to be activated.

* * * * *